United States Patent
Agnihotri et al.

(10) Patent No.: US 9,792,414 B2
(45) Date of Patent: Oct. 17, 2017

(54) METHOD AND DEVICE FOR CASE-BASED DECISION SUPPORT

(75) Inventors: Lalitha Agnihotri, Hartsdale, NY (US); Lilla Boroczky, Mount Kisco, NY (US); Luyin Zhao, Lawrenceville, NJ (US); Michael Chun-chieh Lee, Bronx, NY (US)

(73) Assignee: Koninklijke Philips N.V., Eindhoven (NL)

( * ) Notice: Subject to any disclaimer, the term of this patent is extended or adjusted under 35 U.S.C. 154(b) by 185 days.

(21) Appl. No.: 12/747,535

(22) PCT Filed: Dec. 11, 2008

(86) PCT No.: PCT/IB2008/055218
§ 371 (c)(1),
(2), (4) Date: Jun. 11, 2010

(87) PCT Pub. No.: WO2009/083844
PCT Pub. Date: Jul. 9, 2009

(65) Prior Publication Data
US 2010/0281037 A1    Nov. 4, 2010

Related U.S. Application Data

(60) Provisional application No. 61/015,473, filed on Dec. 20, 2007.

(51) Int. Cl.
*G06F 7/00* (2006.01)
*G06F 19/00* (2011.01)

(52) U.S. Cl.
CPC .................. *G06F 19/345* (2013.01)

(58) Field of Classification Search
CPC ............. G06F 19/345; G06F 17/30522; G06F 19/705; G06F 17/30648; G06F 19/32; G06F 3/0484; G06F 17/3079
(Continued)

(56) References Cited

U.S. PATENT DOCUMENTS 5,893,095 A * 4/1999 Jain .................. G06F 17/30256
5,930,783 A * 7/1999 Li et al.
(Continued)

FOREIGN PATENT DOCUMENTS

CN    1967526 A    5/2007
JP    H10228475 A    8/1998
(Continued)

OTHER PUBLICATIONS

Mikael Sollenborn, "Clustering and Case-Based Reasoning for User Stereotypes", Licentiate Thesis Proposal, Undated, pp. 1-12.
(Continued)

*Primary Examiner* — Mohammed R Uddin

(57) ABSTRACT

This invention relates to a method and device for case-based decision support. It proposes that a case-based decision support system is trained on inputs from several radiologists in order to have a "baseline" system, and then the system provides an option to a radiologist to refine the baseline system based on his/her inputs which either refine weights of features for similarity distance computation directly or provide new similarity ground truth clusters. By enabling modifying the similarity distance computation based on user inputs, this invention adapts similarity ground truth to different users with different experience and/or different opinions.

20 Claims, 3 Drawing Sheets

(58) Field of Classification Search
USPC .......... 707/749, 748, 722, 765, 999.003
See application file for complete search history.

(56) References Cited

U.S. PATENT DOCUMENTS

| | | | |
|---|---|---|---|
| 6,292,577 B1 | 9/2001 | Takahashi | |
| 6,463,432 B1* | 10/2002 | Murakawa | |
| 6,480,840 B2* | 11/2002 | Zhu et al. | |
| 7,490,085 B2 | 2/2009 | Walker et al. | |
| 7,574,422 B2 | 8/2009 | Guan et al. | |
| 7,859,543 B2 | 12/2010 | Salvador | |
| 8,560,551 B2 | 10/2013 | Yoshio et al. | |
| 2002/0065460 A1 | 5/2002 | Murao | |
| 2003/0103663 A1 | 6/2003 | Li et al. | |
| 2004/0024758 A1 | 2/2004 | Iwasaki | |
| 2004/0059215 A1 | 3/2004 | Nishimura et al. | |
| 2004/0181554 A1* | 9/2004 | Heckerman et al. | 707/104.1 |
| 2004/0193036 A1* | 9/2004 | Zhou | G06Q 50/22 600/407 |
| 2005/0020903 A1* | 1/2005 | Krishnan et al. | 600/407 |
| 2005/0049497 A1* | 3/2005 | Krishnan et al. | 600/437 |
| 2005/0059876 A1* | 3/2005 | Krishnan et al. | 600/407 |
| 2005/0149360 A1* | 7/2005 | Galperin | 705/2 |
| 2005/0251013 A1* | 11/2005 | Krishnan et al. | 600/407 |
| 2006/0074290 A1* | 4/2006 | Chen et al. | 600/407 |
| 2006/0120584 A1 | 6/2006 | Hillman | |
| 2006/0218522 A1* | 9/2006 | Hanechak | 717/105 |
| 2007/0122005 A1* | 5/2007 | Kage et al. | 382/115 |
| 2007/0136336 A1* | 6/2007 | Shanahan et al. | 707/101 |
| 2007/0288432 A1* | 12/2007 | Weltman et al. | 707/3 |
| 2008/0005771 A1* | 1/2008 | Salvador | 725/105 |
| 2008/0095418 A1* | 4/2008 | Moriya | 382/128 |
| 2008/0120339 A1* | 5/2008 | Guan et al. | 707/104.1 |
| 2009/0052768 A1 | 2/2009 | Zhao | |
| 2010/0204143 A1 | 8/2010 | Bacher et al. | |
| 2010/0281037 A1 | 11/2010 | Agnihotri et al. | |

FOREIGN PATENT DOCUMENTS

| | | |
|---|---|---|
| JP | 2001052024 A | 2/2001 |
| JP | 2003000575 A | 1/2003 |
| JP | 2003298792 A | 10/2003 |
| JP | 2007279942 A | 10/2007 |
| RU | 2251965 C2 | 5/2005 |
| WO | 2005001740 A2 | 6/2005 |
| WO | 2006054248 A2 | 5/2006 |
| WO | 2007144854 A2 | 12/2007 |

OTHER PUBLICATIONS

Lei Zheng et al, "Design and Analysis of a Content-Based Pathology Image Retrieval System", IEEE Transactions on Information Technology in Biomedicine, vol. 7, No. 4, Dec. 2003, pp. 249-255.

Svetlana Cojocaru et al, "Decision Support System in Ultrasound Investigations", International Conference <<Knowledge-Dialogue-Solutions>>, 2007, pp. 1-7.

"Computer-Aided Diagnosis: Breast Imaging", Duke Advanced Imaging Laboratories, Downloaded May 25, 2010, 1 Page.

Kyoung-Mi Lee, "Cluster-Driven Refinement for Content-Based Digital Image Retrieval", IEEE Transactions on Multimedia, vol. 6, No. 6 Dec. 2004, pp. 817-827.

Yuan Zhong et al, "Perceived Similarity and Visual Descriptions in Content-Based Image Retrieval", Multimeida Workshops, Ninth IEEE International Symposium on Multimedia, 2007, pp. 173-178.

M. Emre Celebi et al, "Content-Based Image Retrieval Incorporating Models of Human Perception", Information Technology: Coding and Computing, vol. 2, 2004, pp. 241-245.

Kakimoto, T., "Electronics, information and communication engineers. D-1, and information systems, 1, information processing and electronic information communication Association", electronic information communication society paper Journal No. J82-D-I, No. 1. 19990125, pp. 130-139.

Hagita, N. The outside one: 'multimedia computing [Vl • finish]' den Joint child-information communication society Journal vol. 80, No. 10, 19971025, p. 1050-1055, Japan electronic information Information communication Association.

* cited by examiner

METHOD AND DEVICE FOR CASE-BASED DECISION SUPPORT

CROSS REFERENCE TO RELATED APPLICATIONS

This application claims the benefit of U.S. provisional application Ser. No. 61/015,473 filed Dec. 20, 2007, which is incorporated herein by reference.

FIELD OF THE INVENTION

The invention relates to case-based decision support, and more particularly, to a method and device for use in personalizing case-based decision support, for example in medical applications such as computer-aided diagnosis (CADx).

BACKGROUND OF THE INVENTION

Radiologists have to read many images of scans produced by computed tomography (CT), X-rays, magnetic resonance imaging (MRI), ultrasound, positron emission tomography (PET), etc. This may lead to "information overload" for radiologists. On the other side, radiologists may misinterpret scans thus leading to delays in treatment or unnecessary biopsies. Information overload potentially aggravates this problem. In such situations, decision support systems such as computer-aided diagnosis schemes are, as a consequence, increasingly being utilized to improve both workflow and patient outcome.

The background of computer-aided diagnosis systems is that clinicians acquire knowledge by experience in referring to cases that they have seen before. One way in which a decision support system can assist a clinician in making a diagnosis of, for example a CT scan of lung cancer, is to offer previous images that have been diagnosed and are similar to the new one. The scan can be generated by the same or any other modalities, such as X-rays, magnetic resonance imaging (MRI), ultrasound, positron emission tomography (PET), etc. An example-based (i.e. case-based) paradigm is that nodules with known diagnosis are retrieved from a database of prior cases and presented to the radiologist. This is the basic premise of an example-based CADx system.

WO patent application, entitled as "Clinician-driven example-based computer-aided diagnosis", filed by Koninklijke Philips Electronics N.V with application number as IB2007/052307 and not published yet, describes a method and device for optimizing clinician-driven example-based computer-aided diagnosis system. According to the WO patent application, optimizing example-based (i.e. case-based) diagnosis is accomplished by clustering volumes-of-interest (VOIs) in a database into respective clusters according to subjective assessment of similarity. An optimal set of volume-of-interest features is then selected for fetching examples such that objective assessment of similarity, based on the selected features, clusters the database VOIs in a feature space so as to conform to the subjective-based clustering. The fetched examples are displayed alongside the VOI to be diagnosed for comparison by the clinician.

SUMMARY OF THE INVENTION

So far, for most existing case-based decision support systems, such as CADx systems, it is assumed that what is similar for one radiologist will also be similar for another radiologist. However, since similarity is very subjective, it is likely that it will differ between different physicians even with the same experience level. Therefore, there is a need to develop reliable similarity metrics for retrieval that are personalized for each user. The problem of finding the similarity is related to the problem of establishing the ground truth of similarity. In decision support, the term "ground truth" typically describes the "correct answer" which an ideal system would return. For example, in a computer-aided diagnosis system that estimates whether a lung nodule is benign or malignant, the ground truth for a data set is the clinically verified diagnosis for each lung nodule: it is either benign, or it is malignant, often proven by a biopsy sample and histopathology analysis. Unlike the ground truth for malignant or benign, the similarity ground truth is fuzzy and not black and white, and is different for each user. Different radiologists may have different opinions on similarity. Thus, the goal is still to create a computer system that can match the ground truth; however, the ground truth itself is much less well-defined. The similarity is highly subjective and changes from user to user. For example, a user may find a fountain pen and a ball-point pen to be similar given that they both write. However, for another user these are two very different objects with completely different properties.

It is proposed herein that a case-based decision support system is trained on inputs from several radiologists in order to establish a "baseline" system, and then the system provides an option to a radiologist to refine the baseline system based on his/her inputs. These inputs are used to either refine weights of features for the similarity distance computation directly or provide new similarity ground truth clusters so as to adapt the similarity distance computation to different users with different experience and/or different opinions.

Therefore, in accordance with one aspect of the present invention, a method is provided that comprises the steps of:
 performing a similarity distance computation between an input case and a set of cases in the database to retrieve similar cases by using a default set of features and weights for assessment of similarity;
 presenting the similar cases and the default set of features and weights to a user;
 receiving from the user, input including a modified weight for at least one of the set of default features and/or at least one new feature in addition to the default set of features; and
 modifying the similarity distance computation with the new set of features and weights for retrieving cases similar for the user.

By enabling modification of weights for features or including new features for similarity distance computation, the proposed method changes system performance directly, and thus adapts similar case retrieval for different users with different experience and/or different opinion.

In an embodiment, the method further comprises steps of receiving input ratings given by the user to a number of cases for similarity clustering, and generating a new set of features and weights based on the similarity clustering to modify the similarity distance computation by running a learning algorithm.

By enabling incorporation of altered ground truth determined by the user and generation of a new set of features and weights for modifying the similarity distance computation, the proposed method changes system performance indirectly, and thus also adapts similarity ground truth to different users with different experience and/or different opinion.

In another embodiment, the method further comprises a step of generating a new set of features and weights as a new baseline for similarity distance computation based on a plurality of personal settings for features and weights collected from a group of users.

In this way, a new baseline is set to be specific for a group of users, for instance specific for a hospital. Further, the difference between each user's personal settings and the new baseline ground truth is evaluated so as to identify the outliers. In the case inexperienced users may want to learn from experienced ones and they should be encouraged to use settings from experienced ones.

In accordance with another aspect of the present invention, a device is provided that comprises:
- a retrieving unit arranged for performing the similarity distance computation between an input case and a set of cases to retrieve similar cases by using a default set of features and weights for assessment of similarity;
- a presenting unit arranged for presenting the similar cases and the default set of features and weights to a user;
- a receiving unit arranged for receiving from the user input including a modified weight for at least one of the set of default features or at least one new feature in addition to the default set of features; and
- a modifying unit arranged for modifying the similarity distance computation with the new set of features and/or weights for retrieving cases similar for the user.

In an embodiment, the receiving unit is further arranged for receiving input ratings given by the user to a number of cases for similarity clustering, and the modifying unit is arranged for generating a new set of features and weights based on the similarity clustering to modify the similarity distance computation by running a learning algorithm.

Modifications and variations thereof, of the inventions defined in independent claims, which correspond to modifications of the method and variations thereof, being described, can be carried out by a skilled person on the basis of the present description.

DESCRIPTION OF THE DRAWINGS

The above and other objects and features of the present invention will become more apparent from the following detailed description considered in connection with the accompanying drawings, in which.

The same reference numerals are used to denote similar parts throughout the figures.

DETAILED DESCRIPTION

Figure 1:
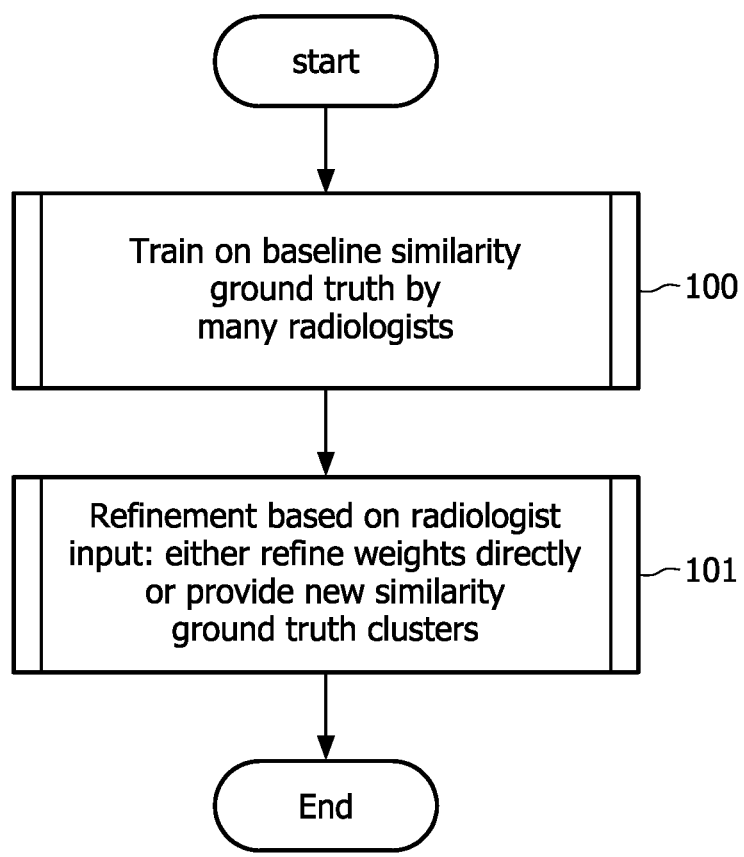
FIG. 1 is a flowchart providing an overview of an exemplary embodiment of the method in accordance with the invention.

FIG. 1 is a flowchart providing an overview of one example of the method according to the invention. According to this method, a case-based decision support system is first trained on inputs from several radiologists in order to establish a "baseline" system (step 100). The system is then adapted for a particular radiologist by a refinement process based on the input of the radiologist (step 101).

The baseline training may occur either during product development or during installation at a hospital by a training module embedded in the system, for example using the method described in the WO patent application IB2007/052307. Once the system is trained for a "general" population, a default set of features and weights used for similarity distance computation is determined. These features and weights are used for objective assessment of similarity between cases to be diagnosed (i.e. cases to be queried) and cases in a database.

When a radiologist first logs into the system he/she has the option to personalize the ground truth and the similarity function for his/her own use with the refinement process provided by the invention. The refinement of similarity ground truth and the similarity function is based on the radiologist's inputs, which may modify the weights of features directly or provide new similarity ground truth clusters or a combination of both. When the radiologist is satisfied with the retrieval results based on the refined ground truth and similarity function after a number of iterations, the refinement process stops and the system is now personalized for the particular radiologist that will retrieve relevant similar cases as perceived by the radiologist.

Figure 2:
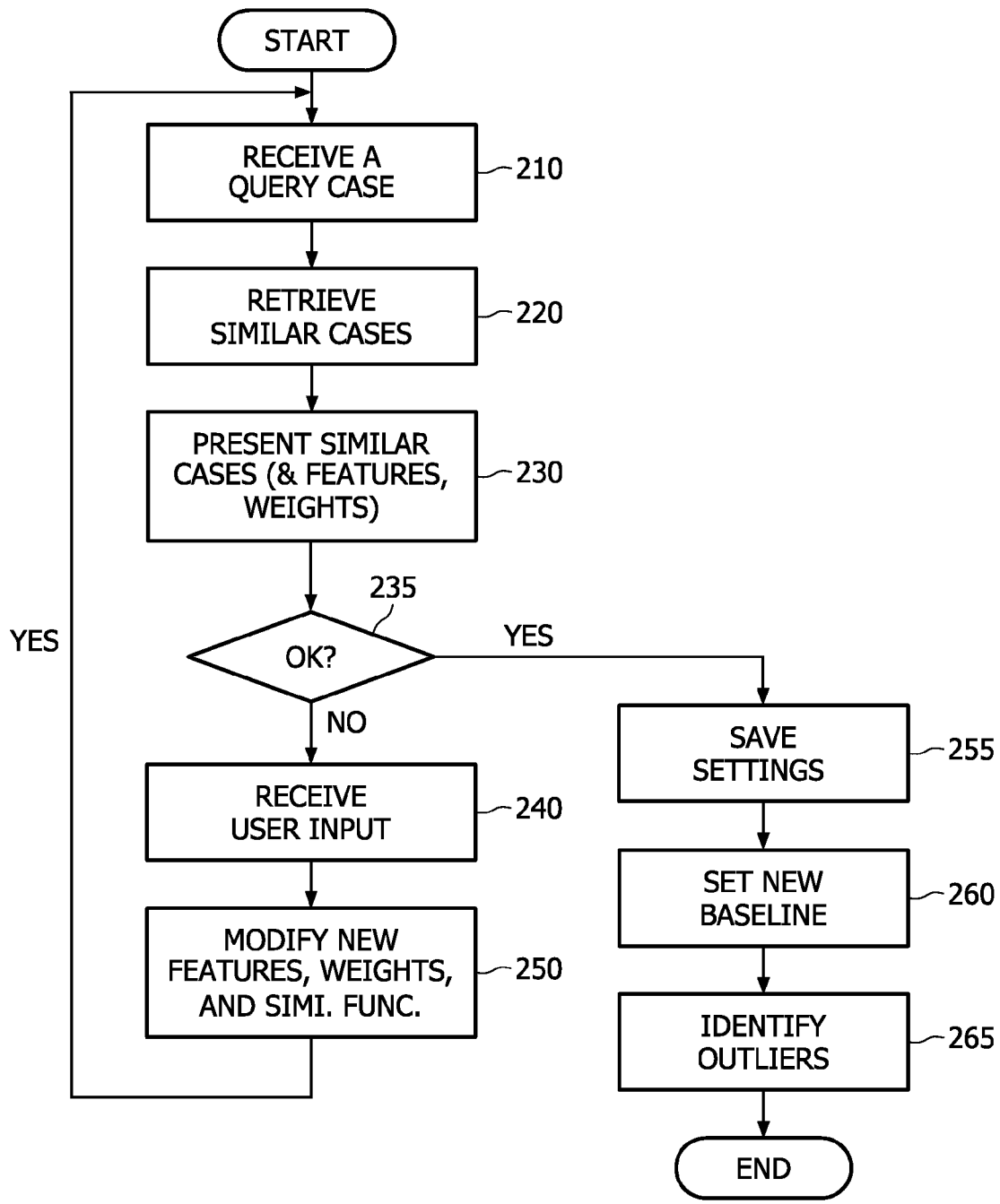
FIG. 2 is a flowchart showing an exemplary embodiment of the refinement process in the method in accordance with the invention.

FIG. 2 is a flowchart showing an exemplary embodiment that elaborates the refinement process, e.g. the step 101 in FIG. 1. It is assumed that a case-based decision support system has been developed and trained as described above. According to FIG. 2, the method comprises a step 210 of receiving a query case from a user, who may be a radiologist, physician or a new resident doctor.

Then the method further comprises a step 220 of performing a similarity distance computation between the input case and a set of cases in the database. Similar cases are retrieved by using a default set of features and weights for assessment of similarity.

Every case, i.e. the images and information associated with a medical subject, is associated with a set of features that characterize that case. These feature may include such characteristics as effective diameter, degree of circularity, contrast, mean gray value, angularity, margin, density, pixel standard deviation, radial gradient index, etc. Clinical data particular to the patient, such as age, cancer history, etc., may also constitute a feature. By a "default set of features", we mean the list of the types of features have been determined in advance, but for every case, there are clearly different values associated with each feature. The default features and their corresponding weights are used for similarity distance computation for objective assessment of the similarity between a case in the query and the cases that are stored in the database as selected by the user. When the features or weights change, i.e. the similarity distance computation changes, the system performance, i.e. the retrieved results, will change accordingly.

The similar cases may be retrieved from a hospital's own databases including cases that have been previously evaluated, diagnosed, or treated at that hospital, from a user's own records including cases that are marked as diagnosed by that particular user, or from a pre-selected training set including cases packaged with the baseline system. The case queried by the user and the cases retrieved from the database may include images and/or text. For example, the case queried by the user can be a diagnostic image (or a series of image) of a medical subject, such as a lung nodule, and the retrieved cases can be lung nodules that have been diagnosed as malignant or benign. The query case and the retrieved results can be further enriched with texts, such as information from an Electronic Health Record of either the query case or the retrieved cases.

The method further comprises a step 230 of presenting the similar cases and the default set of features and weights, which are used in the similarity distance computation for objective assessment of the similarity between the queried case and cases in the database selected by the user, to a user for his/her subjective assessment.

The method further comprises a step 235 of receiving an input from the user indicating whether further adaptation is need. The user views and evaluates the retrieved similar cases and determines whether or not he/she wants to refine the baseline system. If the user is satisfied with the retrieved results (i.e. the similarity ground truth or the similarity distance computation is adequately adapted for the user), then the system does not need further adaptation. Otherwise, the user has the option to adapt the system to his/her needs.

The method further comprises a step 240 of receiving from the user input including a modified weight for at least one of the set of default features or at least one new feature in addition to the default set of features. The user input reflects the user's personal opinion or preference on similarity between cases. In an embodiment, the user may explicitly modify the default features and/or weights. For example, the user inputs information that will modify the weight for an existing feature in the baseline system, or add a new feature, for instance the size change of the tumor due to treatment, which was excluded from the baseline system.

In an alternative embodiment, the modification of features may be done implicitly by a training session. For example, the system may receive the input in terms of an altered ground truth: a different set of cases, for instance a set of lung nodules images, different from the ones initially used in the baseline system, which are to be classified by the user as being similar or not, to a given query case. Alternatively, the user may be presented a series of lung nodules and he/she will rate which are similar and which are not. The user may also indicate which features derived from the cases are used for the clustering. In this way, the user creates a new similarity ground truth that he/she prefers.

The method further comprises a step 250 of modifying the similarity distance computation with the new set of features and weights for retrieving cases similar for the user. When the weights for features are directly modified or new features are directly added by user input, the similarity distance computation will change by using the new set of features and weights, resulting in changes of system performance directly.

When the ground truth is modified, a new set of features and weights will be generated based on input from the user, i.e. the similarity clustering, to modify the similarity function by running a learning algorithm. With the new set of features and weights, the similarity distance computation will change, resulting in changes of system performance indirectly.

The details of how to generate or select a set of new features and weights may refer to the description in patent application WO IB2007/052307, in which a genetic algorithm (GA) is utilized to find an optimal feature space, and, preferably, an optimal point-to-point similarity criterion for use in the optimal feature space. The optimal feature space is to be derived from a pool of features whose member features may be derived from the subjective ranking of features in step of clustering. The pool of features may more inclusively contain any extractable image features, or relevant clinical data, pertaining to the VOIs in the database. Candidate similarity criteria may differ from one another only with respect to the point-to-point distance metric utilized.

Each time a new chromosome is created by reproduction in the GA, fitness of the chromosome is evaluated. Since each chromosome represents a respective set of features and preferably a respective distance metric, and since the fittest chromosome is chosen at the time the stopping criterion is satisfied, each evaluation of chromosome fitness can be considered an iteration of an iterative process. Iteratively, then, a set of features and, preferably, a distance metric is chosen.

Once the set of features and weights for the similarity function is changed, the user may further query the system using a query case. The query case may be the same one used in previous query or a new one input by the user. In such situation, the similar distance computation will be performed using the new set of features and weights that reflect the user's personal similarity ground truth, i.e. the user's opinion on similarity between cases. In this situation, the refinement process goes back to step S110 for further query.

According to the query case received and the updated set of features and weights, the similarity distance computation is performed again for assessment of similarity between the queried case and the cases in database in order to retrieve cases similar for the user. The retrieved cases are presented to the user with the new features and weights used for the similarity distance computation. The user may view and assess the retrieved similar cases again and determine whether further refinement is needed. If the user is still not satisfied with the retrieved result, he/she may make the system again execute the refinement process. After a number of iterations of the refinement process, the user might be satisfied with the retrieved cases and the system is now refined or personalized for the user.

Once the similarity ground truth is adapted for the user, the process goes to step S155, in which the user saves the settings, i.e. the updated features and weights, for use at a later time. A user may be allowed to have more than one set of personalization settings, for use in different application area, to set flags to allow or restrict access of his/her own settings for use by other users and to download his personal settings to his/her computer as needed.

It is advantageous that an embodiment of the method allows all the retrieved cases to change in real-time so that the user can easily fine-tune the retrievals, and allows the user to view two or more sets of queries and retrieved results while adjusting the weights. Further, the refinement process may provide additional control for an experienced user, for example, modifying the weights of features manually or semi-automatically.

It is also advantageous in the above embodiments that the method comprises a step of personalizing by the user the number of cases retrieved and the data or image that they would like to see for each retrieved case, i.e. what clinical information they would like to be presented. At any point during the refinement process or during use of the system, the user may further personalize the system by indicating that a particular case should never be retrieved when he/she is using the system, because, for instance the user has concluded that it is an "atypical" case.

The refinement process may be executed the first time a user logs in or at any time in the future at his/her discretion. For example, it may be desirable to change the personalization settings, i.e. the features and weights used for similarity distance computation, as the user gains more experience.

In another embodiment, the method further comprises step 160 of generating (260) a new set of features and weights as a new baseline for similarity distance computation. The step of generating of new set of features and weights is based on a plurality of personal settings for features and weights collected from a group of users, for instance a group physician using the system in a hospital. The personal setting for features and weights could be set explicitly by direct modification of features/weights or implicitly through a training session, and the new baseline can be set specific for the hospital.

In step 165 of evaluating, the difference between the new baseline and each user's personal settings is calculated so as to identify outliers. In the case inexperienced users may want to learn from experienced ones and they should be encouraged to use settings from experienced ones.

The above method as illustrated in FIGS. 1 and 2 can be implemented with software or hardware, or in combination of both.

Figure 3:
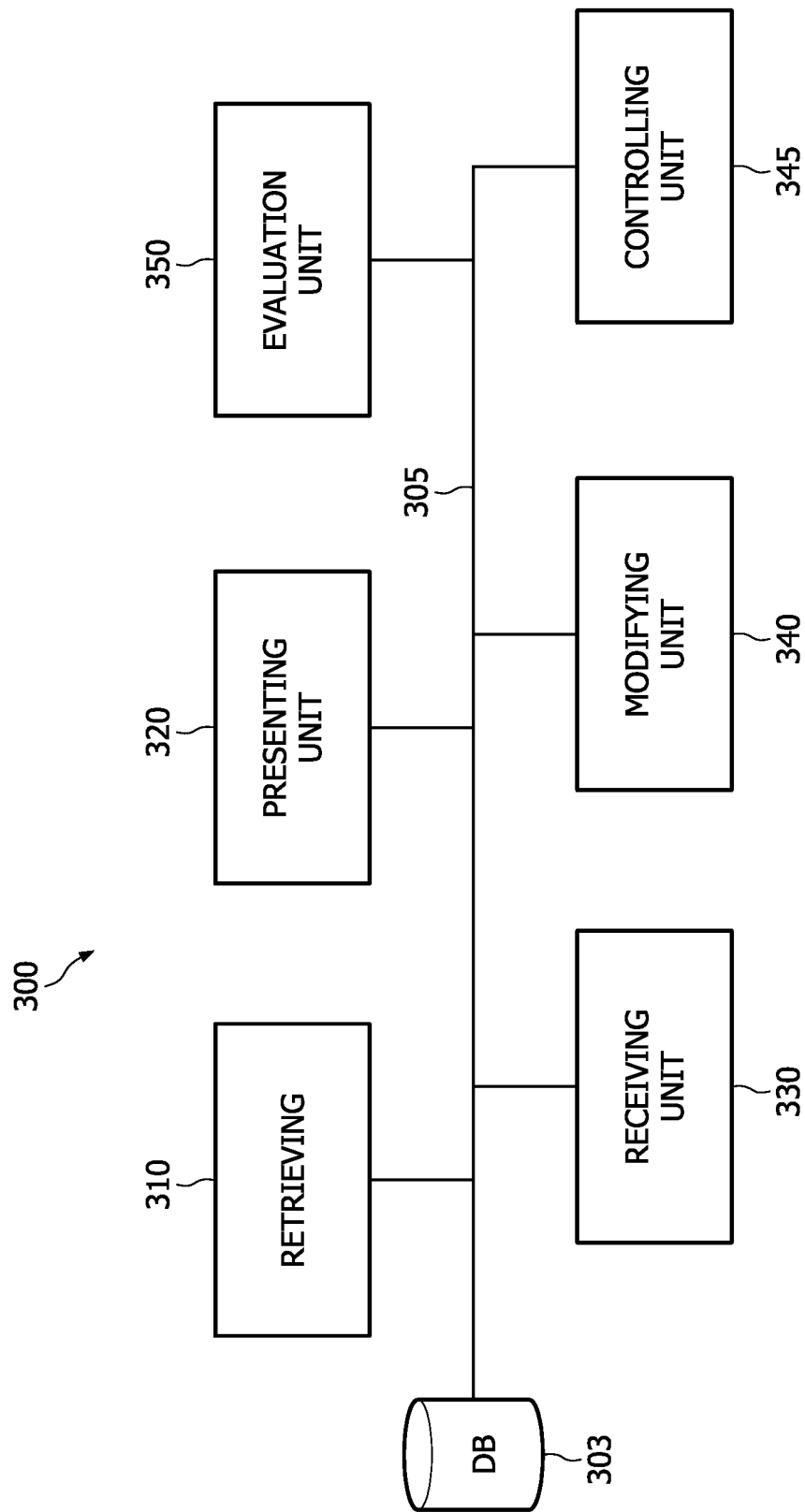
FIG. 3 is a block diagram showing an exemplary embodiment of a device 300 in accordance with the invention.

FIG. 3 is a block diagram showing an exemplary embodiment of a personalized case-based decision support device 300 according to the invention. The device 300 comprises:
- a retrieving unit 310 arranged for performing a similarity distance computation between an input query case and a set of cases from a database to retrieve similar cases using a default set of features and weights for assessment of similarity, i.e. intended to carry out the function of step of retrieving 220;
- a presenting unit 320 arranged for presenting the similar cases and the default set of features and weights to a user, i.e. intended to carry out the function of step of presenting 230;
- a receiving unit 330 arranged for receiving from the user input including a modified weight for at least one of the set of default features or at least one new feature in addition to the default set of features, i.e. intended to carry out the function of step of receiving 240; and
- a modifying unit 340 arranged for modifying the similarity distance computation with the new set of features and weights for retrieving cases similar for the user, i.e. intended to carry out the function of step of modifying 250.

The device 300 may also comprise a database 303 including cases for retrieval and an internal bus 305 for collecting the units in the device 300.

In an embodiment, the receiving unit 330 is further arranged to receive input ratings given by the user to a number of cases for similarity clustering and further receive input of features that the user used for the similarity clustering.

In another embodiment, the modifying unit 340 is arranged to generate a new set of features and weights based on the similarity clustering to modify the similarity distance computation by running a learning algorithm.

In a further embodiment, the device 300 further comprises a controlling unit 345 arranged for controlling an iterative step, in which similarity distance computation is performed by using an updated set of features and weights for retrieving cases similar for the user.

In a further embodiment the device 300 further comprises an evaluating unit 350 arranged for generating a new set of features and weights as a new baseline for similarity distance computation based on a plurality of personal settings for features and weights collected from a group of users. The evaluating unit 350 is further arranged for evaluating the difference between the new baseline and each user's personal settings for features and weights so as to identify outliers.

The skilled person in the art will appreciate that the invention may be enhanced with other functions, such as flexible user interface and authentication control. The invention may be integrated into radiology informatics or healthcare informatics products as a feature or as a separate add-on module. The invention may also be implemented as a stand-alone case-based CADx workstation product.

The invention can be used for a computer aided diagnosis system in conjunction with any imaging modalities. In particular, the invention can be used for assisting diagnosis of different diseases or for confirming suspected diagnoses during the diagnosis process performed by radiologists. Other applications include teaching, emergency diagnosis and case-based computer aided therapy management.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by unit of hardware comprising several distinct elements and by unit of a programmed computer. In the device claims enumerating several units, several of these units can be embodied by one and the same item of hardware or software. The usage of the words first, second and third, et cetera, does not indicate any ordering. These words are to be interpreted as names.

The invention claimed is:

1. A method comprising the steps of:
   performing a similarity distance computation between an input query case and a set of cases to retrieve a first subset of similar cases by using a default set of features and weights for assessment of similarity,
      wherein each feature comprises a case characterization and each weight corresponds to a feature;
   presenting the first subset of similar cases and the default set of features and weights to a user;
   receiving first input from the user, including:
      an indication of a number of cases to be retrieved;
      an indication of specific data or a specific image to be presented with each retrieved case; and
      an indication of a specific case to exclude from retrieval;
   (i) receiving second input from the user, including:
      an indication that an adaptation to the set of features and weights is needed, and at least one of (a) a modified weight for at least one of the default set of features, wherein the user directly modifies the weight or (b) at least one new feature in addition to the default set of features, wherein the user directly adds the new feature;
   (ii) modifying the similarity distance computation with the at least one new feature, and modified weights for retrieving a second subset of similar cases for the user;
   (iii) presenting the retrieved second subset of similar cases with the specific data or specific image for each retrieved case;
   repeating steps (i)-(iii) until receiving third input from the user indicating acceptance.

2. A method as claimed in claim 1 further comprising the steps of:
   receiving input ratings given by the user to a number of cases for similarity clustering;

generating a new set of features and weights based on the similarity clustering to modify the similarity distance computation by running a learning algorithm.

3. A method as claimed in claim 2, before the step of generating, further comprising a step of receiving input of features the user used for the similarity clustering.

4. A method as claimed in claim 2, wherein the learning algorithm is a genetic algorithm.

5. A method as claimed in claim 1 further comprising a step of receiving an input from user for excluding a case from retrieved similar cases for the user.

6. A method as claimed in claim 1 further comprising a step of generating a new set of features and weights as a new baseline for similarity distance computation based on a plurality of personal settings for features and weights collected from a group of users.

7. A method as claimed in claim 6 further comprising a step of evaluating the difference between the new baseline and each user's personal settings for features and weights so as to identify outliers.

8. A method as claimed in claim 1, comprising a step of selecting cases from a database or from a pre-selected training set including cases packaged with the baseline system.

9. The method of claim 1, wherein the similarity distance computation is modified in real-time.

10. The method of claim 1, wherein presenting the retrieved second subset of similar cases includes displaying, at a single time, two or more sets of retrieved similar cases for the user.

11. The method of claim 1, wherein the default set of features and weights is derived from inputs provided by a plurality of healthcare professionals.

12. The method of claim 1, wherein the set of cases are stored in an internal hospital database.

13. The method of claim 1, wherein the set of cases are retrieved from pre-selected training set including cases packaged with a baseline system.

14. The method of claim 1, wherein the set of features includes at least 3 of the following features: an effective diameter, a degree of circularity, a contrast, a mean grey value, an angularity, a margin, a density, a pixel standard deviation, and a radial gradient index.

15. A processing device including a non-transitory computer-readable storage medium and comprising:
  a retrieving unit arranged for performing similarity distance computation between an input query case and a set of cases to retrieve a first subset of similar cases using a default set of features and weights for assessment of similarity,
  wherein each feature comprises a case characterization and each weight corresponds to a feature;
  a presenting unit arranged for presenting the first subset of similar cases and the default set of features and weights to a user;
  a receiving unit arranged for receiving first input from the user, including:
    an indication of a number of cases to be retrieved;
    an indication of specific data or a specific image to be presented with each retrieved case; and
    an indication of a specific case to exclude from retrieval;
    (i) receiving second input from the user, including:
    an indication that an adaptation to the set of features and weights is needed, and at least one of (a) a modified weight for at least one of the default set of features, wherein the user directly modifies the weight or (b) at least one new feature in addition to the default set of features, wherein the user directly adds the new feature; and
    (ii) a modifying unit arranged for modifying the similarity distance computation with the at least one new feature and-modified weights by providing a new similarity ground truth for retrieving a second subset of similar cases for the user;
    (iii) presenting the retrieved second subset of similar cases with the specific data or specific image for each retrieved case;
  repeating steps (i)-(iii) until receiving third input from the user indicating acceptance.

16. A processing device as claimed in claim 15, wherein the receiving unit is further arranged for receiving input ratings given by the user to a number of cases for similarity clustering.

17. A processing device as claimed in claim 16, wherein the receiving unit is further arranged for receiving input of features that the user used for the similarity clustering.

18. A processing device as claimed in claim 16, wherein the modifying unit is arranged for generating a new set of features and weights based on the similarity clustering to modify the similarity distance computation by running a learning algorithm.

19. A processing device as claimed in claim 15, further comprising a controlling unit arranged for controlling an iterative step, in which similarity distance computation is performed by using an updated set of features and weights for retrieving the second subset of similar cases for the user.

20. A processing device as claimed in claim 19, further comprising an evaluating unit arranged for generating a new set of features and weights as a new baseline for similarity distance computation based on a plurality of personal settings for features and weights collected from a group of users.

* * * * *